US00PP24266P2

(12) United States Plant Patent
Yamaguchi

(10) Patent No.: US PP24,266 P2
(45) Date of Patent: Feb. 25, 2014

(54) ***BEGONIA* PLANT NAMED 'SUNJIRAORE'**

(50) Latin Name: *Begonia×tuberhybrida*
Varietal Denomination: Sunjiraore

(75) Inventor: Hideki Yamaguchi, Narusawa-mura (JP)

(73) Assignee: Suntory Flowers Ltd., Tokyo (JP)

( * ) Notice: Subject to any disclaimer, the term of this patent is extended or adjusted under 35 U.S.C. 154(b) by 136 days.

(21) Appl. No.: 13/385,533

(22) Filed: Feb. 23, 2012

(51) Int. Cl.
*A01H 5/00* (2006.01)

(52) U.S. Cl.
USPC ..... Plt./347

(58) Field of Classification Search
USPC ..... Plt./347, 349, 344
See application file for complete search history.

*Primary Examiner* — June Hwu
(74) *Attorney, Agent, or Firm* — C. A. Whealy

(57) ABSTRACT

A new and distinct cultivar of *Begonia* plant named 'Sunjiraore', characterized by its compact, outwardly spreading and mounding plant habit; vigorous growth habit; freely branching habit; and numerous single orange red-colored flowers that are held above and beyond the foliar plane.

1 Drawing Sheet

Botanical designation: *Begonia×tuberhybrida.*
Cultivar denomination: 'SUNJIRAORE'.

BACKGROUND OF THE INVENTION

The present invention relates to a new and distinct cultivar of *Begonia* plant, botanically known as *Begonia×tuberhybrida* and hereinafter referred to by the name 'Sunjiraore'.

The new *Begonia* plant is a product of a planned breeding program conducted by the Inventor in Narusawa-mura, Minamituru-gun, Yamanashi, Japan. The objective of the breeding program is to create new compact and freely branching *Begonia* plants with a mounding plant habit and attractive leaf and flower coloration.

The new *Begonia* plant originated from a cross-pollination made by the Inventor in Narusawa-mura, Minamituru-gun, Yamanashi, Japan in May, 2005 of a proprietary selection of *Begonia×tuberhybrida* identified as code number FC02Or3304Or31-1, not patented, as the female, or seed, parent with a proprietary selection of *Begonia×tuberhybrida* identified as code number FC02Or3604Or31-2, not patented, as the male, or pollen, parent. The new *Begonia* plant was discovered and selected by the Inventor as a single flowering plant from within the progeny of the stated cross-pollination in a controlled environment in Narusawa-mura, Minamituru-gun, Yamanashi, Japan in August, 2006.

Asexual reproduction of the new *Begonia* plant by cuttings taken in a controlled greenhouse environment in Narusawa-mura, Minamituru-gun, Yamanashi, Japan since October, 2006 has shown that the unique features of this new *Begonia* plant are stable and reproduced true to type in successive generations.

SUMMARY OF THE INVENTION

Plants of the new *Begonia* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Sunjiraore'. These characteristics in combination distinguish 'Sunjiraore' as a new and distinct *Begonia* plant:

1. Compact, outwardly spreading and mounding plant habit.
2. Vigorous growth habit.
3. Freely branching habit.
4. Numerous single orange red-colored flowers that are held above and beyond the foliar plane.

Plants of the new *Begonia* differ primarily from plants of the female parent selection in the following characteristics:

1. Plants of the new *Begonia* have larger leaves than plants of the female parent selection.
2. Plants of the new *Begonia* have larger male flowers than plants of the female parent selection.

Plants of the new *Begonia* differ primarily from plants of the male parent selection in the following characteristics:

1. Plants of the new *Begonia* have larger leaves than plants of the male parent selection.
2. Plants of the new *Begonia* have larger male flowers than plants of the male parent selection.

Plants of the new *Begonia* can be compared to plants of *Begonia×tuberhybrida* 'Firecracker Orange', not patented. In side-by-side comparisons conducted in Narusawa-mura, Minamituru-gun, Yamanashi, Japan, plants of the new *Begonia* differed primarily from plants of 'Firecracker Orange' in the following characteristics:

1. Plants of the new *Begonia* had shorter internodes than plants of 'Firecracker Orange'.
2. Plants of the new *Begonia* had shorter leaves and leaf petioles than plants of 'Firecracker Orange'.
3. Plants of the new *Begonia* and 'Firecracker Orange' differed in leaf and leaf petiole color.
4. Plants of the new *Begonia* were more freely flowering than plants of 'Firecracker Orange'.
5. Plants of the new *Begonia* had smaller female flowers than plants of 'Firecracker Orange'.
6. Plants of the new *Begonia* and 'Firecracker Orange' differed in flower color as plants of 'Firecracker Orange' had slightly darker orange red-colored flowers.

7. Plants of the new *Begonia* had shorter peduncles than plants of 'Firecracker Orange'.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph at the top of the sheet comprises a side perspective view of a typical flowering plant of 'Sunjiraore' grown in a container.

The photograph at the bottom of the sheet is a close up view of a typical flower of 'Sunjiraore'.

DETAILED BOTANICAL DESCRIPTION

The aforementioned photographs and following observations and measurements describe plants grown during the late spring/early summer in 12-cm containers in a polyethylene-covered greenhouse in Higashiomi, Shiga, Japan under commercial practices. During the production of the plants, the day temperatures averaged 23° C. and the night temperatures averaged 13° C. Plants were four months old when the photographs and description were taken. In the following description, color references are made to The Royal Horticultural Society Colour Chart, 2007 Edition, except where general terms of ordinary dictionary significance are used.

Botanical classification: *Begonia×tuberhybrida* 'Sunjiraore'.

Parentage:

*Female, or seed, parent.*—Proprietary selection of *Begonia×tuberhybrida* identified as code number FC02Or3304Or31-1, not patented.

*Male, or pollen, parent.*—Proprietary selection of *Begonia×tuberhybrida* identified as code number FC02Or3604Or31-2, not patented.

Propagation:

*Type.*—By cuttings.

*Time to initiate roots, summer.*—About 15 days at temperatures of 17° C. to 28° C.

*Time to initiate roots, winter.*—About 20 days at temperatures of 14° C. to 23° C.

*Time to produce a rooted young plant, summer.*—About 40 days at temperatures of 17° C. to 28° C.

*Time to produce a rooted young plant, winter.*—About 50 days at temperatures of 14° C. to 23° C.

*Root description.*—Fine, fibrous; white in color.

*Rooting habit.*—Freely branching; plants of the new *Begonia* have been observed to form tubers during the winter.

Plant description:

*Plant form and growth habit.*—Compact and mounding plant habit, outwardly spreading; freely branching with good stem strength; flowers are single and positioned above and beyond the foliar plane; vigorous growth habit.

*Plant height.*—About 24 cm.

*Plant width.*—About 27.8 cm.

*Lateral branches.*—Length: About 18.8 cm. Diameter: About 3 mm. Internode length: About 2.3 cm. Aspect: Upright to outwardly. Texture: Sparsely pubescent. Color: Close to 175A.

*Leaves.*—Arrangement: Alternate; simple. Length: About 9.6 cm. Width: About 3.5 cm. Shape: Lanceolate, asymmetrical. Apex: Acute. Base: Cordate. Margin: Serrate. Texture, upper and lower surfaces: Smooth, glabrous. Venation pattern: Palmate. Color: Developing leaves, upper surface: Close to 152A. Developing leaves, lower surface: Close to 182B. Fully expanded leaves, upper surface: Close to 137B; venation, close to 144B. Fully expanded leaves, lower surface: Close to 147C; venation, close to 145A. Petioles: Length: About 2 cm. Diameter: About 1.9 mm. Texture, upper and lower surfaces: Sparsely pubescent. Color, upper and lower surfaces: Close to 178B. Stipules: Length: About 5.2 cm. Width: About 2.4 cm. Shape: Narrowly ovate. Apex: Acute. Base: Truncate. Margin: Entire. Texture, upper and lower surfaces: Smooth, glabrous. Color, upper and lower surfaces: Close to 138D.

Flower description:

*Flowering habit.*—Single flowers arranged in axillary cymes; usually about three to four flowers per cyme and about 18 cymes developing per plant; flowers positioned above and beyond the foliar plane; flowers pendulous.

*Natural flowering season.*—Plants begin flowering about six to seven weeks planting; in the garden, plants flower continuously from the spring to late autumn in Japan; flowers not persistent.

*Fragrance.*—None detected.

*Male flowers buds.*—Length: About 2.8 cm. Diameter: About 9.6 mm. Shape: Ovoid. Color: Close to 32A.

*Male flowers.*—Shape: Cruciform. Diameter: About 4.5 cm. Depth (height): About 4.2 cm. Tepals: Quantity and arrangement: Four per flower in a single whorl. Length: About 3.8 cm. Width: About 1.3 cm. Shape: Ovate to lanceolate. Apex: Acute. Base: Obtuse. Margin: Entire. Texture, upper and lower surfaces: Smooth, glabrous. Color: When opening and fully opened, upper surface: Close to 32A. When opening and fully opened, lower surface: Close to 32A.

*Female flowers buds.*—Length: About 1.7 cm. Diameter: About 6.3 mm. Shape: Ovoid. Color: Close to 32A.

*Female flowers.*—Shape: Rounded. Diameter: About 3.3 cm. Depth (height): About 2.4 cm. Tepals: Quantity and arrangement: Five or six per flower in a single whorl. Length: About 2.7 cm. Width: About 7.3 mm. Shape: Lanceolate. Apex: Acute. Base: Obtuse. Margin: Entire. Texture, upper and lower surfaces: Smooth, glabrous. Color: When opening and fully opened, upper surface: Close to 32A. When opening and fully opened, lower surface: Close to 32A.

*Flower bracts.*—Length: About 7.2 mm. Width: About 6.8 mm. Color: Close to 144B; towards the apex, close to 179A to 179B.

*Peduncles.*—Angle: Outwardly. Length: About 2.7 cm. Diameter: About 1.7 mm. Texture: Smooth, glabrous. Color: Close to N199D tinted with close to 178C.

*Pedicels.*—Angle: Drooping. Length: About 2.4 cm. Diameter: About 1.6 mm. Texture: Smooth, glabrous. Color: Close to N199D tinted with close to 178C.

*Reproductive organs.*—Stamens: Quantity: About 28 per male flower. Length: About 1.8 cm. Anther shape: Ovoid. Anther length: About 1.6 mm. Anther diameter: About 0.8 mm. Anther color: Close to 17A and 12D. Pollen amount: Moderate. Pollen color: Close to 12D. Pistils: Quantity: One per female flower. Length: About 1.2 cm. Stigma shape: Six-lobed, convoluted. Stigma color: Close to 25A and 17B. Style color: Close to 25A and 17B. Ovary length: About 8.8 mm. Ovary diameter: About 1.8 cm. Ovary color: Close to 144B and 34B.

*Seeds and fruits.*—Seed and fruit production have not been observed on plants of the new *Begonia.*

Postproduction longevity: Excellent postproduction longevity, plants last about 220 days.

Disease & pest resistance: Resistance to pathogens and pests common to *Begonias* has not been observed.

Temperature tolerance: Plants of the new *Begonia* have been observed to tolerate temperatures from about 14° C. to about 28° C.

It is claimed:

1. A new and distinct *Begonia* plant named 'Sunjiraore' as illustrated and described.

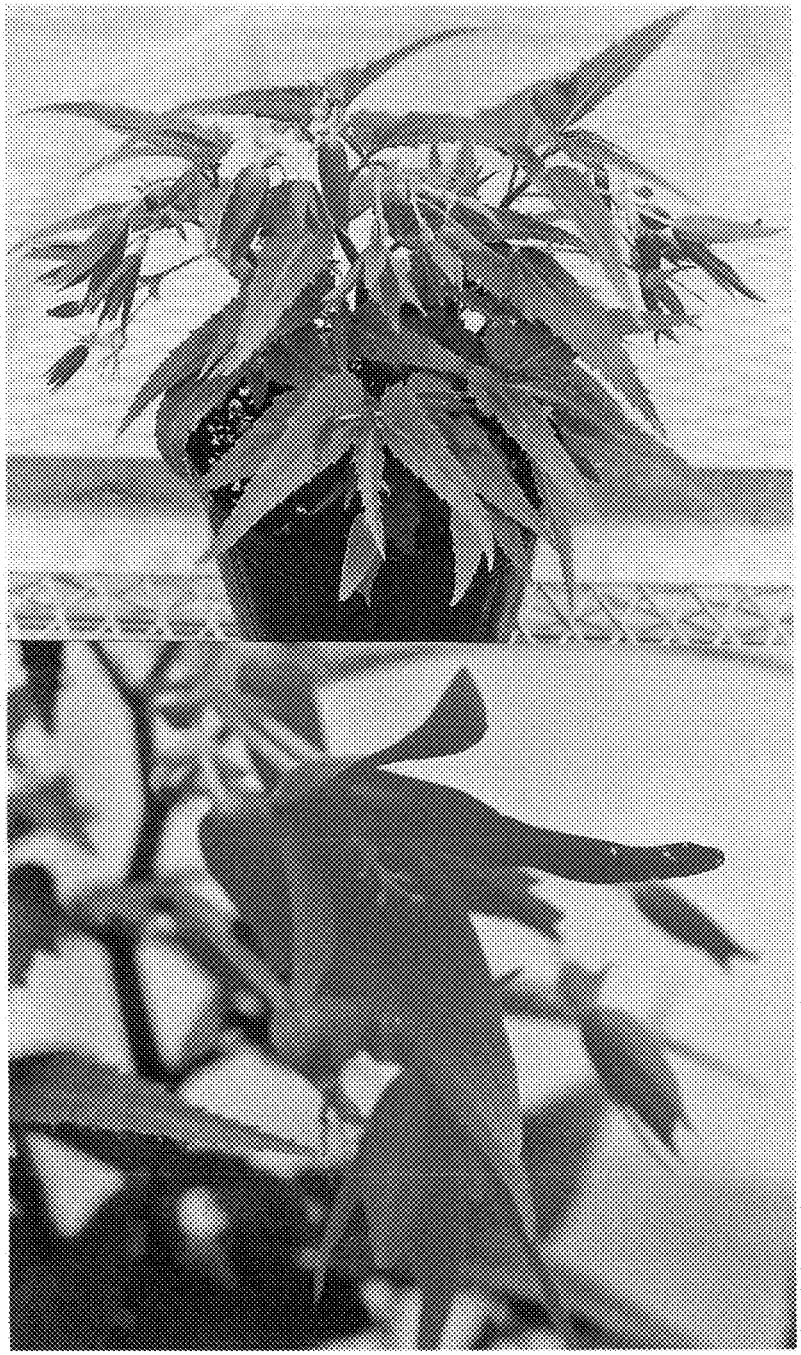

* * * * *